(12) United States Patent
Akiyama et al.

(10) Patent No.: US 8,691,548 B2
(45) Date of Patent: Apr. 8, 2014

(54) ASYMMETRIC HYDROLASE AND GENE THEREOF

(71) Applicant: Sumitomo Chemical Company, Limited, Tokyo (JP)

(72) Inventors: Toshihiko Akiyama, Osaka (JP); Norihiko Hirata, Osaka (JP); Shinji Hourai, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/718,566

(22) Filed: Dec. 18, 2012

(65) Prior Publication Data

US 2013/0177963 A1    Jul. 11, 2013

(30) Foreign Application Priority Data

Dec. 19, 2011 (JP) ................. 2011-277193

(51) Int. Cl.
*C12N 9/14* (2006.01)
(52) U.S. Cl.
USPC .......................................................... 435/195
(58) Field of Classification Search
USPC .......................... 435/195, 252.2, 69.1, 320.1
See application file for complete search history.

(56) References Cited

U.S. PATENT DOCUMENTS

2010/0240107 A1    9/2010   Hirata et al.

FOREIGN PATENT DOCUMENTS

| JP | 3875283 B2 | 11/2006 |
| WO | WO 02/102790 A1 | 12/2002 |
| WO | WO 2008/140127 A1 | 11/2008 |

OTHER PUBLICATIONS

European Search Report for corresponding European Patent Application No. 12197683.1. dated Mar. 7, 2013.
Barrow et al., "Total Synthesis of Cryptophycins. Revision of the Structures of Cryptophycins A and C," J. Am. Chem. Soc., vol. 117, pp. 2479-2490, 1995.
Bentley et al., "Tributyltin hydride-mediated radical cyclisation of carbonyls to form functionalised oxygen and nitrogen heterocycles," J. Chem. Soc., Perkin Transl. 1. pp. 1461-1469, 2002.

*Primary Examiner* — Tekchand Saidha
*Assistant Examiner* — Rama P Ramanujam
(74) *Attorney, Agent, or Firm* — Birch, Stewart, Kolasch & Birch, LLP

(57) ABSTRACT

The present invention relates to, for example, an α-substituted β-amino acid ester derivative asymmetric hydrolase including an enzyme of the following (a) or (b):

(a) an enzyme comprising the amino acid sequence of SEQ ID NO:1 at least from position 1 to position 362, wherein the tyrosine at position 277 of SEQ ID NO:1 is substituted with alanine, tryptophan, isoleucine, or histidine, and having the ability to hydrolyze a substrate; or (b) an enzyme comprising the amino acid sequence of SEQ ID NO:1 at least from position 1 to position 362, wherein the tyrosine at position 277 of SEQ ID NO:1 is substituted with an amino acid other than tyrosine, and having the ability to hydrolyze a substrate.

8 Claims, No Drawings

ASYMMETRIC HYDROLASE AND GENE THEREOF

This application claims priority to and the benefit of Japanese Patent Application No. 2011-277193, filed Dec. 19, 2011, the entire contents of which is incorporated herein by reference.

TECHNICAL FIELD

The present invention relates to an enzyme which is applicable to asymmetric hydrolysis of an α-substituted β-amino acid ester derivative, a polynucleotide encoding the enzyme, and others.

BACKGROUND ART

An optically active α-substituted β-amino acid derivative is useful as a raw material and an intermediate for producing pharmaceutical bulk compounds, agricultural chemicals or biologically active substances. For example, Patent Document 1 discloses optically active α-substituted β-amino acid derivatives which are used as materials for production of antimicrobial agents. Also, Non Patent Documents 1 and 2 disclose optically active α-substituted β-amino acid derivatives which are used as intermediates for production of cytotoxic depsipeptide cryptophycin.

Hydrolases have an ability to hydrolyze a substrate and in recent years, have been used in organic synthesis reaction for producing, for example, compounds which are used as active ingredients of pharmaceuticals or agricultural chemicals, or intermediates thereof. Particularly, hydrolases have been used in organic synthesis reaction for producing optically active compounds or intermediates thereof. For example, an enzyme having the amino acid sequence of SEQ ID NO: 1 and having an ability to hydrolyze a substrate has been known as a hydrolase (see e.g., Patent Document 2).

It is desirable that such industrially applicable hydrolases for producing optically active compounds or intermediates thereof, etc., have the following properties: ability to produce hydrolysis reaction product having high optical purity; ability to highly recognize the absolute configuration of the substrate; high stability against various reaction conditions such as temperature, pH, solvents or pressure; and so on. Particularly, if the reaction product has a high optical purity (i.e., the optical selectivity of the hydrolase is high), a purification step is not needed after the enzymatic reaction so that optically active compounds can be synthesized with favorable productivity.

CITATION LIST

Patent Document

Patent Document 1: WO 02/102790
Patent Document 2: Japanese Patent No. 3875283

Non Patent Document

Non-Patent Document 1: J. Am. Chem. Soc. 1995, 117, 2479
Non-Patent Document 2: J. Chem. Soc., Perkin Trans. 1, 2002, 1461

SUMMARY OF THE INVENTION

For the purpose of reducing reaction steps and improving productivity, there has been a strong demand for the development of a hydrolase having high optical selectivity.

The present invention provides, for example, a hydrolase having excellent optical selectivity and a polynucleotide encoding the enzyme.

In exemplary embodiments, the present invention provides the following 1)-8):

1) an enzyme of the following (a) or (b) (hereinafter, sometimes referred to as the enzyme of the present invention):
(a) an enzyme comprising the amino acid sequence of SEQ ID NO:1 at least from position 1 to position 362, wherein the tyrosine at position 277 of SEQ ID NO:1 is substituted with alanine, tryptophan, isoleucine, or histidine, and having an ability to hydrolyze a substrate; or
(b) an enzyme comprising the amino acid sequence of SEQ ID NO:1 at least from position 1 to position 362, wherein the tyrosine at position 277 of SEQ ID NO:1 is substituted with an amino acid other than tyrosine,
and having an ability to hydrolyze a substrate;
2) a polynucleotide comprising a nucleotide sequence encoding the amino acid sequence of the enzyme according to 1) (hereinafter, sometimes referred to as the polynucleotide of the present invention);
3) a vector comprising the polynucleotide according to 2) (hereinafter, sometimes referred to as the vector of the present invention);
4) a transformant into which the polynucleotide according to 2) has been introduced (hereinafter, sometimes referred to as the transformant of the present invention);
5) a transformant comprising the vector according to 3);
6) a method for producing an enzyme, comprising culturing the transformant according to 4) or 5);
7) a method for modifying an enzyme comprising the amino acid sequence of SEQ ID NO:1, comprising a step of substituting the tyrosine at position 277 in the amino acid sequence of SEQ ID NO:1 with alanine, tryptophan, isoleucine, or histidine (hereinafter, sometimes referred to as the enzyme modification method of the present invention); and
8) a method for modifying a polynucleotide comprising a nucleotide sequence encoding the amino acid sequence of SEQ ID NO:1, comprising a step of substituting the tyrosine-encoding codon at positions 829 to 831 in the nucleotide sequence encoding the amino acid sequence of SEQ ID NO:1 with a codon encoding alanine, tryptophan, isoleucine, or histidine (hereinafter, sometimes referred to as the polynucleotide modification method of the present invention).

According to the present invention, can be provided a hydrolase having excellent optical selectivity or the like, which may be used in an organic synthesis reaction for producing an optically active compound that is available for an active ingredient in pharmaceuticals or agricultural chemicals, or an intermediate of the optically active compound, such as optically active α-substituted β-amino acid derivatives.

DESCRIPTION OF EMBODIMENTS

Hereinafter, the present invention is explained more specifically.

As used herein, the enzyme of the present invention may be described as a combination of a position number in the amino acid sequence of SEQ ID NO:1 and one letter of alphabet representing an amino acid. For example, "277I" means an enzyme comprising an amino acid sequence equivalent to the amino acid sequence of SEQ ID NO: 1 except that it has an amino acid mutation where the tyrosine at position 277 of SEQ ID NO: 1 is substituted with isoleucine.

With regard to the enzyme of the present invention, "ability to hydrolyze a substrate" (hereinafter, sometimes referred to as hydrolase activity) can be determined, for example, by mixing the enzyme with its substrate such as α-substituted β-amino acid ester derivative (specifically, e.g., 2-n-butyl-3-[(N-benzyloxy-N-formyl)amino]propanoic acid ethyl ester) in the presence of water, subsequently incubating the mixture at 25° C., and then quantifying the optical purity and chemical purity of an α-substituted (β-amino acid derivative (specifically, e.g., 2-n-butyl-3-[(N-benzyloxy-N-formyl)amino]propanoic acid) in the obtained reaction solution by means of high-performance liquid chromatography.

The enzyme of the present invention is an enzyme characterized by the following (a) or (b):
(a) an enzyme comprising the amino acid sequence of SEQ ID NO:1 at least from position 1 to position 362, wherein the tyrosine at position 277 of SEQ ID NO:1 is substituted with alanine, tryptophan, isoleucine, or histidine, and having the ability to hydrolyze a substrate; or
(b) an enzyme comprising the amino acid sequence of SEQ ID NO:1 at least from position 1 to position 362, wherein the tyrosine at position 277 of SEQ ID NO:1 is substituted with an amino acid other than tyrosine, and having the ability to hydrolyze a substrate.

An enzyme of the amino acid sequence of SEQ ID NO: 1 (hereinafter referred to as the wild-type hydrolase) is a *Chromobacterium* SC-YM-1 strain (FERM BP-6703)-derived hydrolase known in the art. When the wild-type hydrolase is produced in recombinant *E. coli*, in addition to the full-length hydrolase, a truncated hydrolase that lacks eight C-terminal amino acids of the full-length hydrolase is produced. The truncated hydrolase has hydrolytic activity, and its C-terminal amino acid is Glu corresponding to Glu at position 362 in the amino acid sequence of SEQ ID NO:1. Thus, the enzyme of the present invention may have an amino acid sequence which corresponds to at least from position 1 to position 362 of the amino acid sequence of SEQ ID NO: 1.

"an amino acid other than tyrosine" as described above refers to any amino acid excluding tyrosine from 20 kinds of amino acids constituting a protein, including glycine, alanine, valine, leucine, isoleucine, serine, threonine, cysteine, methionine, aspartic acid, glutamic acid, asparagine, glutamine, lysine, arginine, histidine, proline, phenylalanine or tryptophane. Preferably, "an amino acid other than tyrosine" as described above refers to alanine, tryptophane, isoleucine or histidine.

Specific examples of the enzyme of the present invention include the following enzymes:
an enzyme essentially consisting of the amino acid sequence of SEQ ID NO:1 from position 1 to position 362 wherein the tyrosine at position 277 of SEQ ID NO:1 is substituted with alanine, and having an ability to hydrolyze a substrate;
an enzyme comprising the amino acid sequence of SEQ ID NO:1 wherein the tyrosine at position 277 of SEQ ID NO:1 is substituted with alanine, and having an ability to hydrolyze a substrate;
an enzyme essentially consisting of the amino acid sequence of SEQ ID NO:1 from position 1 to position 362 wherein the tyrosine at position 277 of SEQ ID NO:1 is substituted with tryptophane, and having an ability to hydrolyze a substrate;
an enzyme comprising the amino acid sequence of SEQ ID NO:1 wherein the tyrosine at position 277 of SEQ ID NO:1 is substituted with tryptophane, and having an ability to hydrolyze a substrate;
an enzyme essentially consisting of the amino acid sequence of SEQ ID NO:1 from position 1 to position 362 wherein the tyrosine at position 277 of SEQ ID NO:1 is substituted with isoleucine, and having an ability to hydrolyze a substrate;
an enzyme comprising the amino acid sequence of SEQ ID NO:1 wherein the tyrosine at position 277 of SEQ ID NO:1 is substituted with isoleucine, and having an ability to hydrolyze a substrate;
an enzyme essentially consisting of the amino acid sequence of SEQ ID NO:1 from position 1 to position 362 wherein the tyrosine at position 277 of SEQ ID NO:1 is substituted with histidine, and having an ability to hydrolyze a substrate; and
an enzyme comprising the amino acid sequence of SEQ ID NO:1 wherein the tyrosine at position 277 of SEQ ID NO:1 is substituted with histidine, and having an ability to hydrolyze a substrate.

For obtaining the polynucleotide comprising a nucleotide sequence encoding the amino acid sequence of the enzyme of the present invention, for example, the following method may be used.

Firstly, a polynucleotide comprising a nucleotide sequence encoding the amino acid sequence of the wild-type hydrolase (hereinafter, sometimes referred to as the wild-type polynucleotide) is obtained. Examples of a nucleotide sequence encoding the amino acid sequence of SEQ ID NO:1 include the nucleotide sequence of SEQ ID NO: 10 or SEQ ID NO:11.

The wild-type polynucleotide can be obtained from the *Chromobacterium* SC-YM-1 strain (deposited under the deposit number of FERM BP-6703 in International Patent Organism Depositary (IPOD), National Institute of Technology and Evaluation (NITE), Tsukuba Central 6, 1-1-1, Higashi, Tsukuba, Ibaraki 305-8566, Japan in 15 Apr., 1999 in accordance with Budapest Treaty) according to conventional genetic engineering techniques described in, for example, J. Sambrook, E. F. Fritsch, T. Maniatis; Molecular Cloning 2nd edition, Cold Spring Harbor Laboratory, 1989. Specifically, genomic DNA is extracted from the *Chromobacterium* SC-YM-1 strain according to a conventional method. For example, the bacterial cells are disrupted by a conventional method such as ultrasonic homogenization, followed by protease treatment or the like and subsequently extracting genomic DNA. The obtained genomic DNA is cleaved with appropriate restriction enzymes and inserted into, for example, a phage vector λgt11 or a plasmid vector pUC19 using ligase, thereby preparing a genomic DNA library. The wild-type polynucleotide can be obtained from the obtained genomic DNA library by a screening method, for example, an immunological method using an antibody against the wild-type hydrolase, a hybridization method using a synthetic DNA probe corresponding to a partial amino acid sequence of the wild-type hydrolase, or a method for assaying the activity of the wild-type hydrolase. Alternatively, the wild-type polynucleotide can also be prepared by performing PCR using appropriate primers, thereby amplifying the polynucleotide comprising a nucleotide sequence encoding the amino acid sequence of SEQ ID NO:1.

The obtained wild-type polynucleotide can be mutated by site-directed mutagenesis as shown below, thereby preparing the polynucleotide of the present invention. The site-directed mutagenesis method is a method where a variant polynucleotide (i.e. the polynucleotide of the present invention) is synthesized using a single-stranded DNA of an original polynucleotide (i.e. the wild-type polynucleotide)-incorporated plasmid as a template and synthetic oligonucleotides comprising a nucleotide sequence to be mutated as primers. In the present invention, primers for mutagenesis may be prepared to perform amplification by a PCR method so that the amino acid at position 277 in the amino acid sequence of SEQ ID NO:1 can be substituted with an amino acid other than tyrosine. Preferable is a specific mutation in which the amino acid at position 277 is substituted with alanine, tryptophan, isoleucine, or histidine.

In this context, examples of the "site-directed mutagenesis method" can include the methods of Olfert Landt et al. (Gene 96, 125-128, 1990), Smith et al. (Genetic Engineering 3, 1, Setlow, J. and Hollaender, A, Plenum: New York), Vlasuk et al. (Experimental Manipulation of Gene Expression, Inouye, M.: Academic Press, New York), and Hos. N. Hunt et al. (Gene 77, 51, 1989), and use of commercially available kits such as Mutan-Express Km (manufactured by Takara Shuzo Co., Ltd.), TaKaRa La PCR in vitro Mutagenesis Kit (manufactured by Takara Shuzo Co., Ltd.), and QuikChange II Site-Directed Mutagenesis Kit (manufactured by Stratagene Corp.).

Specifically, to prepare the polynucleotide encoding a hydrolase that comprises the amino acid sequence of SEQ ID NO:1 at least from position 1 to position 362 wherein the tyrosine at position 277 of SEQ ID NO:1 is substituted with an amino acid other than tyrosine, using, for example, the method of Olfert Landt et al. (Gene 96, 125-128, 1990), a wild-type gene-incorporated vector (DNA) is firstly prepared according to a method described in, for example, J. Sambrook, E. F. Fritsch, T. Maniatis; Molecular Cloning 2nd edition, Cold Spring Harbor Laboratory, 1989.

Subsequently, the obtained vector (DNA) is used as a template to amplify a DNA fragment by a PCR method using, for example, an oligonucleotide comprising a nucleotide sequence encoding an amino acid sequence in which the tyrosine at position 277 of SEQ ID NO: 1 is substituted with alanine, tryptophan, isoleucine, or histidine (e.g., an oligonucleotide comprising the nucleotide sequence of SEQ ID NO:2) as a sense primer and an oligonucleotide comprising the nucleotide sequence complementary to the sense primer (e.g., an oligonucleotide comprising the nucleotide sequence of SEQ ID NO:3) as an antisense primer. In this context, examples of conditions for the PCR reaction can include conditions involving incubation at 95° C. for 1 minute and subsequent 12 cycles of incubation treatment at 95° C. for 50 seconds, then 55° C. for 1 minute, and 68° C. for 5 minutes, and finally incubation at 4° C. A DpnI restriction enzyme is added to the PCR reaction solution containing the amplified DNA fragment, and then incubated at 37° C. for 1 hour, followed by transformation of E. coli with the resulting solution. The vector can be purified from the obtained transformant, thereby obtaining the polynucleotide of the present invention of interest.

The polynucleotide of the present invention can be also prepared by chemical synthesis of a nucleic acid comprising a desired nucleotide sequence based on its nucleotide sequence according to a conventional method such as phosphite triester method (Hunkapiller, M. et al., Nature, 310, 105, 1984).

For obtaining the enzyme of the present invention, a vector that allows the polynucleotide of the present invention to be expressed in host cells such as microorganisms is prepared, and the vector is introduced into host cells to prepare transformants. Subsequently, the prepared transformants can be cultured according to a conventional cell culture method. In this way, the enzyme of the present invention can be produced and obtained in large amounts.

The vector of the present invention contains the polynucleotide of the present invention.

The vector of the present invention can be constructed by incorporating the polynucleotide of the present invention according to conventional genetic engineering techniques into a vector that can be used in host cells into which the polynucleotide of the present invention is introduced, for example, a vector that contains genetic information replicable in host cells, can autonomously proliferate, can be isolated and purified from the host cells, and has a detectable marker (hereinafter, sometimes referred to as a basic vector).

In this context, examples of the "basic vector" can include a vector pUC119 (manufactured by Takara Shuzo Co., Ltd.) and a phagemid pBluescript II (manufactured by Stratagene Corp.) in the case where E. coli is used as host cells. Moreover, examples of the "basic vector" can include vectors pGBT9, pGAD424, and pACT2 (manufactured by Clontech Laboratories, Inc.) in the case where budding yeasts are used as host cells. Moreover, examples of the "basic vector" can include vectors such as pRc/RSV and pRc/CMV (manufactured by Invitrogen Corp.), vectors containing a virus-derived autonomous replication origin such as a bovine papilloma virus vector pBPV (manufactured by Amersham Pharmacia Biotech Inc.) and an EB virus vector pCEP4 (manufactured by Invitrogen Corp.), and viruses such as vaccinia virus in the case where mammalian cells are used as host cells. Moreover, examples of the "basic vector" can include insect viruses such as baculovirus in the case where insect cells are used as host cells.

When the vector of the present invention is constructed using a vector containing an autonomous replication origin (specifically, e.g., a vector pACT2 for yeasts, a bovine papilloma virus vector pBPV, or an EB virus vector pCEP4), this vector is intracellularly retained as an episome after being introduced into host cells.

Host cells can be transformed by introducing thereinto the vector that allows the polynucleotide of the present invention to be expressed in host cells such as microorganisms to thereby prepare transformants. The prepared transformants can be cultured according to a conventional cell culture method to thereby produce and obtain the enzyme of the present invention in large amounts.

The vector that allows the polynucleotide of the present invention to be expressed in host cells such as microorganisms can be prepared by operably linking a promoter operable in the host cells such as microorganisms to upstream of the polynucleotide of the present invention and incorporating this into the basic vector as described above.

In this context, the phrase "operably linking or operably linked" means that the promoter and the polynucleotide of the present invention are linked so that the polynucleotide of the present invention is expressed under the control of the promoter in the host cells such as microorganisms into which the polynucleotide of the present invention is introduced.

Examples of the promoter operable in the host cells can include DNA that exhibits promoter activity in the host cells to which the polynucleotide of the present invention is transferred. Examples of the promoter operable in the host cells can include E. coli lactose operon promoter (lacP), tryptophan operon promoter (trpP), arginine operon promoter (argP), galactose operon promoter (galP), tac promoter, T7 promoter, T3 promoter, and λ phage promoter (λ-pL and λ-pR) in the case where the host cells are E. coli. Moreover, examples of the promoter operable in the host cells can include Rous sarcoma virus (RSV) promoter, cytomegalovirus (CMV) promoter, simian virus (SV40) early or late promoter, and mouse mammary tumor virus (MMTV) promoter in the case where the host cells are animal cells or fission yeasts. Moreover, examples of the promoter operable in the host cells can include ADH1 promoter (the ADH1 promoter can be prepared by a conventional genetic engineering method from, for example, a yeast expression vector pAAHS [available from Washington Research Foundation; Ammerer et al., Method in Enzymology, 101 part (p. 192-201)] carrying the ADH1 promoter and ADH1 terminator) in the case where the host cells are budding yeasts.

In the case of using a basic vector originally carrying a promoter operable in host cells, the polynucleotide of the present invention can be inserted to downstream of the promoter so that the promoter is operably linked to the polynucleotide of the present invention. In the case of, for example, pRc/RSV or pRc/CMV, a cloning site is provided downstream of the promoter operable in animal cells. A vector obtained by inserting the polynucleotide of the present invention to the cloning site can be introduced into animal cells to thereby allow the polynucleotide of the present invention to be expressed in the animal cells. Since these vectors originally carry SV40 autonomous replication origin (ori), when the vectors are introduced into cultured cells transformed with ori-deficient SV40 genome, for example, COS cells, the copy number of the vectors is largely increased in the cells, and consequently, the polynucleotide of the present invention which has been incorporated into the vectors can be expressed in large amounts. Moreover, the vector pACT2 for yeasts has ADH1 promoter, and the polynucleotide of the present invention can be inserted to downstream of the ADH1 promoter in this vector or its derivative to thereby construct a vector that allows the polynucleotide of the present invention to be expressed in large amounts in budding yeasts, for example, CG1945 (manufactured by Clontech Laboratories, Inc.). Linking the polynucleotide of the present invention to a ribosomal binding site may achieve higher expression. Although the report of Guarente. L et al. (Cell 20, p. 543 (1980)) and the report of Taniguchi et al. (Genetics of Industrial Microorganisms, p. 202 (1982), Kodansha Ltd.) are known as to the ribosomal binding site, a ribosomal binding site suitable for the expression of the polynucleotide of the present invention may be designed and synthesized as desired.

Examples of the host cells can include microorganisms, for example, eukaryotes and prokaryotes. Preferable examples thereof can include *E. coli*. The vector as described above can be introduced into the host cells by a conventional genetic engineering method to thereby transform the host cells.

A conventional transfection method suitable for the host cells can be applied to a method for introducing the vector of the present invention to the host cells. Examples of the transfection method can include conventional methods such as a calcium chloride method and an electroporation method described in, for example, J. Sambrook, E. F. Frisch, T. Maniatis; Molecular Cloning 2nd edition, Cold Spring Harbor Laboratory, 1989 in the case where *E. coli* is used as the host cells. Moreover, examples of the transfection method can include conventional gene transfer methods such as a calcium phosphate method, a DEAE dextran method, an electroporation method, and a lipofection method in the case where mammalian cells or insect cells are used as the host cells. Moreover, examples of the transfection method can include conventional methods such as a lithium method used in, for example, Yeast transformation kit (manufactured by Clontech Laboratories, Inc.) in the case where yeasts are used as the host cells. In the case of using a virus as a vector, the genome of the virus can be introduced into the host cells by the conventional gene transfer method as described above. In addition, the genome of the virus can also be introduced into the host cells by infecting the host cells with a viral particle containing the genome of the virus having an insert of the polynucleotide of the present invention.

For the selection of the transformant of the present invention, for example, the host cells in which a marker gene is introduced together with the vector of the present invention can be cultured by a method suitable for the properties of the marker gene. In the case where the marker gene is, for example, a gene conferring drug resistance to a selection agent that exhibits lethal activity against the host cells, the host cells in which the vector of the present invention is introduced can be cultured using a medium supplemented with the selection agent. Examples of the combination of the drug resistance-conferring gene and the selection agent can include a combination of a neomycin resistance-conferring gene and neomycin, a combination of a hygromycin resistance-conferring gene and hygromycin, and a combination of a Blasticidin S resistance-conferring gene and Blasticidin S. In the case where the marker gene is a gene complementing the auxotrophy of the host cells, the host cells in which the vector of the present invention is introduced can be cultured using a minimal medium free from a nutrient corresponding to the auxotrophy. Moreover, in the case where the vector of the present invention that allows the polynucleotide of the present invention to be expressed in host cells is introduced, a detection method based on the enzymatic activity of the enzyme of the present invention may be used.

For obtaining the transformant of the present invention in which the polynucleotide of the present invention is positioned in the chromosome of the host cell, for example, the vector of the present invention and a vector having a marker gene are firstly linearized by digestion with restriction enzymes or the like, and these are then introduced into host cells by the method described above. Subsequently, the cells are usually cultured for a few weeks. Then, the transformant of interest can be obtained by the selection based on the expression level of the introduced marker gene. Alternatively, for example, the vector of the present invention having the gene conferring resistance to a selection agent as described above as a marker gene is firstly introduced into host cells by the method described above. Subsequently, the cells are subcultured for a few weeks or longer in a medium supplemented with the selection agent. Then, selection agent-resistant clones that have survived in a colony form can also be cultured for purification to thereby select and obtain the transformant of the present invention in which the polynucleotide of the present invention is introduced in the chromosome of the host cell. For confirming the successful integration of the introduced polynucleotide of the present invention in the chromosome of the host cell, the genomic DNA of the cell is prepared according to a conventional genetic engineering method, and the presence of the polynucleotide of the present invention can be detected from the prepared genomic DNA using a method such as PCR or Southern hybridization with DNA comprising a partial nucleotide sequence of the introduced polynucleotide of the present invention as a primer or probe. Since the transformant may be cryopreserved and can be used, if necessary, after being revived, time and labor for transformant preparation for each experiment can be saved and tests can be conducted using the transformant whose properties or handling conditions have been confirmed in advance.

The culture of the transformant containing the polynucleotide of the present invention or the vector of the present invention (i.e., the transformant of the present invention) may be performed by a conventional cell culture method.

In the case where the transformant of the present invention is a microorganisms, for example, the transformant can be cultured using various media appropriately containing a carbon source, a nitrogen source, an organic or inorganic salt, and the like used in the conventional culture of conventional microorganisms.

Examples of the carbon source include: sugars such as glucose, dextrin, and sucrose; sugar alcohols such as glycerol; organic acids such as fumaric acid, citric acid, and pyruvic acid; and animal oils, plant oils, and molasses. The amount of the carbon source added to the medium is usually on the order of 0.1 to 30% (w/v) with respect to the culture solution.

Examples of the nitrogen source include: natural organic nitrogen sources such as meat extracts, peptone, yeast extracts, malt extracts, soybean flour, corn steep liquor, cottonseed flour, dry yeast, and casamino acid; amino acids; sodium salts of inorganic acids, such as sodium nitrate; ammonium salts of inorganic acids, such as ammonium chloride, ammonium sulfate, and ammonium phosphate; ammonium salts of organic acids, such as ammonium fumarate and ammonium citrate; and urea. Of these, the ammonium salts of organic acids, the natural organic nitrogen sources, the amino acids, and the like can also be used as the carbon source in many cases. The amount of the nitrogen source added to the medium is usually on the order of 0.1 to 30% (w/v) with respect to the culture solution.

Examples of the organic salt or inorganic salt can include chloride, sulfate, acetate, carbonate, and phosphate of potassium, sodium, magnesium, iron, manganese, cobalt, zinc, copper, or the like. Specifically, examples thereof include sodium chloride, potassium chloride, magnesium sulfate, ferrous sulfate, manganese sulfate, cobalt chloride, zinc sulfate, copper sulfate, sodium acetate, calcium carbonate, monopotassium hydrogen phosphate, and dipotassium hydrogen phosphate. The amount of the organic salt and/or inorganic salt added to the medium is usually on the order of 0.0001 to 5% (w/v) with respect to the culture solution.

Furthermore, in the case of a transformant in which a gene prepared by operably linking a promoter of allolactose-inducible type such as tac promoter, trc promoter, and lac promoter to the polynucleotide of the present invention is introduced, for example, a small amount of isopropylthio-β-D-galactoside (IPTG) may be added to the medium as an inducer for inducing the production of the enzyme of the present invention.

The culture of the transformant of the present invention may be performed according to a method usually used in the culture of host cells such as microorganisms. Examples of the method include liquid culture and solid culture, such as test tube shaking culture, reciprocal shaking culture, jar fermenter culture, and tank culture.

The culture temperature can be changed appropriately within a range in which the transformant is viable, and is usually approximately 15° C. to approximately 40° C. The pH of the medium is preferably in the range of approximately 6 to approximately 8. The culture time differs depending on culture conditions and is usually preferably approximately 1 day to approximately 5 days.

A method used in conventional protein purification can be applied to a method for purifying the enzyme of the present invention from the cultures of the transformant of the present invention. For example, a method as shown below can be used.

Firstly, cells are collected from the cultures of the transformant by centrifugation or the like, and these are then homogenized by, for example, a physical homogenization method such as sonication, Dyno-mill treatment, or French press treatment, or a chemical homogenization method using a surfactant or a lytic enzyme such as lysozyme. Impurities are removed from the obtained homogenate solution by centrifugation, filtration through a membrane filter, or the like to thereby prepare a cell-free extract solution, which can then be fractionated appropriately using a separation and purification method such as cation-exchange chromatography, anion-exchange chromatography, hydrophobic chromatography, gel filtration chromatography, or metal chelate chromatography to thereby purify the enzyme of the present invention.

Examples of the carrier used in chromatography include insoluble polymer carriers such as cellulose, dextrin, or agarose in which a carboxymethyl (CM) group, a diethylaminoethyl (DEAE) group, a phenyl group, or a butyl group is introduced. A commercially available carrier-packed column may be used. Examples of the commercially available carrier-packed column include Q-Sepharose FF and Phenyl-Sepharose HP (trade names; all manufactured by GE Healthcare Japan), and TSK-gel G3000SW (trade name; manufactured by Tosoh Corp.).

To select the fraction containing the enzyme of the present invention, for example, the selection can be performed on the basis of the presence or absence of the hydrolase activity according to the present invention or the degree thereof. The selection may be performed by assaying the ability to asymmetrically hydrolyze the substrate α-substituted β-amino acid ester derivative (specifically, e.g., 2-n-butyl-3-[(N-benzyloxy-N-formyl)amino]propanoic acid ethyl ester) to preferentially produce the corresponding carboxylic acid.

The α-substituted β-amino acid ester derivative is treated with the enzyme of the present invention or the transformant of the present invention or its processed product to preferentially produce the corresponding optically active carboxylic acid.

The substituent bound to the carbon atom at α-position (hereinafter, abbreviated to α-substituent) of the α-substituted β-amino acid ester derivative is a hydrocarbon group having 1 to 20 carbon atoms. The hydrocarbon group may be any of an aliphatic hydrocarbon group, an alicyclic hydrocarbon group, and an aromatic hydrocarbon group, and combinations thereof. For the hydrocarbon group as the α-substituent, the number of its carbon atoms is preferably 1 to 7, more preferably 3 to 6. The aliphatic hydrocarbon group is typically an alkyl group. Examples thereof include a methyl group, an ethyl group, a propyl group, a butyl group, a pentyl group, a hexyl group, an octyl group, a decyl group, a dodecyl group, a tetradecyl group, a hexadecyl group, an octadecyl group, and an icosyl group, which may be linear or branched. Examples of the alicyclic hydrocarbon group include a cyclobutyl group, a cyclopentyl group, a cyclohexyl group, a cyclooctyl group, a cyclodecyl group, a norbornyl group, and an adamantyl group. The aromatic hydrocarbon group is typically an aryl group. Examples of the aryl group include a phenyl group, a naphthyl group, an anthracenyl group, and a biphenyl group. Also, these hydrocarbon groups as the α-substituent may have a substituent. Examples of the substituent include an alkyl group, an alkoxy group, an aryl group, an aryloxy group, an aralkyloxy group, a halogen atom, a nitro group, and a cyano group.

The α-substituent in the α-substituted β-amino acid ester derivative may be, as described above, a combination of the aliphatic hydrocarbon group and the alicyclic hydrocarbon group, a combination of the aliphatic hydrocarbon group and the aromatic hydrocarbon group, or a combination of the alicyclic hydrocarbon group and the aromatic hydrocarbon group. Examples of the combination of the aliphatic hydrocarbon group and the alicyclic hydrocarbon group typically include a combination of a cycloalkyl group and an alkanediyl group. Specifically, examples thereof include a cyclopentylmethyl group, a cyclopentylethyl group, a cyclopentylpropyl group, a cyclopentylbutyl group, a cyclohexylmethyl group, a cyclohexylethyl group, a cyclohexylpropyl group, a cyclohexylbutyl group, a cyclooctylmethyl group, a cyclooctylethyl group, a cyclooctylpropyl group, and a cyclooctylbutyl group. The combination of the aliphatic hydrocarbon group and the aromatic hydrocarbon group is typically an aralkyl group, and examples thereof include a benzyl group and a naphthylmethyl group. The combination of the alicyclic hydrocarbon group and the aromatic hydrocarbon group is a phenylcyclopentyl group, a phenylcyclohexyl group, a naphthylcyclopentyl group, a naphthylcyclohexyl group, or the like. Also, one α-substituent or two α-substituents different from each other may be bound to the carbon atom at α-position. Preferably one α-substituent is bound thereto.

The α-substituent in the α-substituted β-amino acid ester derivative is described above with reference to its specific examples. Among these, the α-substituent is preferably an aliphatic hydrocarbon group, more preferably methyl, ethyl, n-propyl, a n-butyl group, or a n-pentyl group, particularly preferably a n-butyl group or a n-pentyl group. Intermediate materials for production of biologically active substances such as the α-substituted β-amino acid derivatives described in Non Patent Literatures 1 and 2 above can be obtained easily from the α-substituted β-amino acid ester derivative whose α-substituent is a methyl group or a n-propyl group. Also, optically active compounds serving as active ingredients in pharmaceuticals or agricultural chemicals, or intermediates thereof, such as the α-substituted β-amino acid derivatives described in Patent Literature 1 above can be obtained easily from the α-substituted β-amino acid ester derivative whose α-substituent is a n-butyl group or a n-pentyl group.

The amino group at β-position of the α-substituted β-amino acid ester derivative may have a substituent. Examples of the substituent in the amino group include general amino-protecting groups. The amino-protecting groups can also be selected appropriately with reference to, for example, Greene et al., Protective Groups in Organic Synthesis, 3rd Edition, 1999, John Wiley & Sons, Inc.

The substituent or the amino-protecting group in the amino group refers to, for example, an alkyl group having 1 to 10 carbon atoms which may have a substituent, an alkenyl group having 2 to 10 carbon atoms which may have a substituent, an aralkyl group having 7 to 20 carbon atoms which may have a substituent, an acyl group having 1 to 10 carbon atoms which may have a substituent, an alkoxycarbonyl group having 2 to 15 carbon atoms which may have a substituent, an alkenyloxycarbonyl group having 2 to carbon atoms which may have a substituent, an aralkyloxycarbonyl group having 8 to 20 carbon atoms which may have a substituent, a benzylidene group having 6 to 20 carbon atoms which may have a substituent, a sulfonyl group having 1 to 10 carbon atoms which may have a substituent, a carboxyl group (—COOH), a carboxamide group (—CONH$_2$), a hydroxyl group (—OH), an alkoxy group having 1 to 10 carbon atoms which may have a substituent, an alkenyloxy group having 2 to 10 carbon atoms which may have a substituent, an aralkyloxy group having 7 to 20 carbon atoms which may have a substituent, an aryloxy group having 6 to 20 carbon atoms which may have a substituent, an acyloxy group having 2 to 15 carbon atoms which may have a substituent, an alkoxycarbonyloxy group having 2 to 15 carbon atoms which may have a substituent, an alkenyloxycarbonyloxy group having 2 to 15 carbon atoms which may have a substituent, an aralkyloxycarbonyloxy group having 8 to 20 carbon atoms which may have a substituent, or a cyclic ethenyloxy group having 4 to 10 carbon atoms which may have a substituent.

Examples of the alkyl group include a methyl group, an ethyl group, a propyl group, and a butyl group, which may be linear, branched, or cyclic.

Examples of the alkenyl group include a vinyl group and an allyl group, which may be linear, branched, or cyclic.

Examples of the aralkyl group include a benzyl group, a 4-methoxybenzyl group, a diphenylmethyl group, and a triphenylmethyl group.

Examples of the acyl group include a formyl group, an acetyl group, a chloroacetyl group, a propionyl group, a butyryl group, a pivaloyl group, a benzoyl group, and a phthaloyl group, which may be linear, branched, or cyclic.

Examples of the alkoxycarbonyl group include a methoxycarbonyl group, an ethoxycarbonyl group, a 2,2,2-trichloroethoxycarbonyl group, a propoxycarbonyl group, and a butoxycarbonyl group, which may be linear, branched, or cyclic.

Examples of the alkenyloxycarbonyl group include a vinyloxycarbonyl group and an allyloxycarbonyl group, which may be linear, branched, or cyclic.

Examples of the aralkyloxycarbonyl group include a 9-fluorenylmethyloxycarbonyl group, a benzyloxycarbonyl group, a 4-methoxybenzyloxycarbonyl group, and a 4-nitrobenzyloxycarbonyl group.

Examples of the benzylidene group include a benzylidene group, a 4-methoxybenzylidene group, and a diphenylmethylene group.

Examples of the sulfonyl group include a benzenesulfonyl group, a 4-toluenesulfonyl group, a 2-nitrobenzenesulfonyl group, and a 4-nitrobenzenesulfonyl group.

Examples of the alkoxy group include a methoxy group, an ethoxy group, a propoxy group, and a butoxy group, which may be linear, branched, or cyclic.

Examples of the alkenyloxy group include a vinyloxy group and an allyloxy group, which may be linear, branched, or cyclic.

Examples of the aralkyloxy group include a benzyloxy group and a 4-methoxybenzyloxy group.

Examples of the aryloxy group include a phenoxy group and a naphthyloxy group.

Examples of the aryloxy group include an acetyloxy group, a chloroacetyloxy group, a propionyloxy group, a butyryloxy group, a pivaloyloxy group, and a benzoyloxy group, which may be linear, branched, or cyclic.

Examples of the alkoxycarbonyloxy group include a methoxycarbonyloxy group, an ethoxycarbonyloxy group, a 2,2,2-trichloroethoxycarbonyloxy group, a propoxycarbonyloxy group, and a butoxycarbonyloxy group, which may be linear, branched, or cyclic.

Examples of the alkenyloxycarbonyloxy group include a vinyloxycarbonyloxy group and an allyloxycarbonyloxy group, which may be linear, branched, or cyclic.

Examples of the aralkyloxycarbonyloxy group include a 9-fluorenylmethyloxycarbonyloxy group, a benzyloxycarbonyloxy group, a 4-methoxybenzyloxycarbonyloxy group, and a 4-nitrobenzyloxycarbonyloxy group.

Examples of the cyclic ethenyloxy group include a tetrahydro-2H-pyran-2-yloxy group, a tetrahydrofuran-2-yloxy group, and a 1,4-dioxan-2-yloxy group.

Moreover, the alkyl group, the alkenyl group, the aralkyl group, the acyl group, the alkoxycarbonyl group, the alkenyloxycarbonyl group, the aralkyloxycarbonyl group, the benzylidene group, the sulfonyl group, the alkoxycarbonyl group, the carboxamide group, the alkoxy group, the alkenyloxy group, the aralkyloxy group, the aryloxy group, the acyloxy group, the alkoxycarbonyloxy group, the alkenyloxycarbonyloxy group, the aralkyloxycarbonyloxy group, and the cyclic ethenyloxy group may further have a substituent. The substituent is the same as those exemplified as the hydrocarbon group substituent as the α-substituent.

The amino-protecting group may be substituted with 0, 1, or two substituents. In the case of two substituents, these substituents may be the same as or different from each other.

The substituent in the amino group at β-position is described above with reference to its specific examples. Among these, the substituent in the amino group at f3-position is preferably a hydrogen atom, an acyl group having 1 to 10 carbon atoms, or an aralkyloxy group having 7 to 20 carbon atoms, more preferably a formyl group or a benzyloxy group, particularly preferably a combination of the formyl group and the benzyloxy group.

A substituent other than the amino group bound to the carbon atom at β-position is not particularly limited and is preferably a hydrogen atom.

The group having the ester bond in the α-substituted β-amino acid ester derivative is an alkoxycarbonyl group having 2 to 10 carbon atoms which may have a substituent. The alkoxycarbonyl group may be linear or branched. Moreover, specific examples of the alkoxycarbonyl group are the same as those described for the alkoxycarbonyl group as the substituent or the protecting group in the amino group at β-position within the number of carbon atoms ranging from 2 to 10. For the alkoxycarbonyl group, the number of its carbon atoms is more preferably 2 to 4. A methoxycarbonyl group or an ethoxycarbonyl group is particularly preferable. The optional substituent in the alkoxycarbonyl group is the same as those exemplified as the optional substituent in the α-substituent.

In this context, examples of the preferable α-substituted β-amino acid ester derivative specifically include 2-n-butyl-3-[(N-benzyloxy)amino]propanoic acid methyl ester, 2-n-butyl-3-[(N-benzyloxy)amino]propanoic acid ethyl ester, 2-n-pentyl-3-[(N-benzyloxy)amino]propanoic acid methyl ester, 2-n-pentyl-3-[(N-benzyloxy)amino]propanoic acid ethyl ester, 2-n-butyl-3-[(N-benzyloxy-N-formyl)amino]propanoic acid methyl ester, 2-n-butyl-3-[(N-benzyloxy-N-formyl)amino]propanoic acid ethyl ester, 2-n-pentyl-3-[(N-benzyloxy-N-formyl)amino]propanoic acid methyl ester, and 2-n-pentyl-3-[(N-benzyloxy-N-formyl)amino]propanoic acid ethyl ester. Among them, 2-n-butyl-3-[(N-benzyloxy-N-formyl)amino]propanoic acid methyl ester or 2-n-butyl-3-[(N-benzyloxy-N-formyl)amino]propanoic acid ethyl ester is particularly preferable.

The optical isomer mixture of the α-substituted β-amino acid ester derivative can be obtained by a production method known in the art. This production method is described in, for example, ARKICOV 2010 (iX), p. 196 to 205.

The optically active α-substituted β-amino acid ester derivative may be a racemate or may be a mixture in which optical isomers are mixed at an arbitrary ratio. This racemate or mixture may be prepared freshly or may be used after being resolved.

Examples of the optically active α-substituted β-amino acid derivative obtained by treating the α-substituted β-amino acid ester derivative with the enzyme of the present invention, the transformant of the present invention or its processed product specifically include (R)-2-n-butyl-3-[(N-benzyloxy)amino]propanoic acid, (R)-2-n-pentyl-3-[(N-benzyloxy)amino]propanoic acid, (R)-2-n-butyl-3-[(N-benzyloxy-N-formyl)amino]propanoic acid, and (R)-2-n-pentyl-3-[(N-benzyloxy-N-formyl)amino]propanoic acid, and compounds in which (R) described above is replaced with (S).

When the α-substituted β-amino acid ester derivative is treated with the transformant of the present invention or its processed product to produce the corresponding optically active carboxylic acid, the reaction is usually performed in the presence of water. Water used in this reaction may be a buffered aqueous solution. Examples of the buffer used in the buffered aqueous solution can include: alkali metal salts of phosphoric acid, such as sodium phosphate and potassium phosphate; alkali metal salts of acetic acid, such as an aqueous sodium acetate solution and potassium acetate; and mixtures thereof.

In the reaction, an organic solvent may be allowed to coexist with water. Examples of the organic solvent that may be allowed to coexist can include: ethers such as t-butyl methyl ether, diisopropyl ether, and tetrahydrofuran; esters such as ethyl formate, ethyl acetate, propyl acetate, butyl acetate, ethyl propionate, and butyl propionate; hydrocarbons such as toluene, hexane, cyclohexane, heptane, and isooctane; alcohols such as methanol, ethanol, 2-propanol, butanol, and t-butyl alcohol; organic sulfur compounds such as dimethyl sulfoxide; ketones such as acetone; nitriles such as acetonitrile; and mixtures thereof.

The reaction is performed, for example, by mixing water and the α-substituted β-amino acid ester derivative with the enzyme of the present invention or the transformant or its processed product producing it, if necessary, in a state further containing an organic solvent or the like, by stirring, shaking, or the like.

The pH during the reaction can be selected appropriately and is usually in the range of pH 3 to 10. Moreover, the reaction temperature can be selected appropriately and is usually in the range of 0 to 60° C. in terms of the stability of the material and the product, and reaction rates.

The endpoint of the reaction can be determined, for example, by monitoring the amount of the α-substituted β-amino acid derivative in the reaction solution by liquid chromatography or the like. The reaction time can be selected appropriately and is usually in the range of 0.5 hours to 10 days.

The reaction solution after the completion of the reaction contains the asymmetric hydrolysis reaction product α-substituted β-amino acid derivative and the residual α-substituted β-amino acid ester derivative. For separating them, for example, a method is adopted, which involves performing water/hydrophobic organic solvent extraction operation to distribute the residual α-substituted n-amino acid ester derivative and the α-substituted β-amino acid derivative into an organic layer (hydrophobic organic solvent layer) and an aqueous layer, respectively, and separating between the organic layer and the aqueous layer.

For separating the optically active α-substituted β-amino acid derivative, which is the compound of interest, from the enzyme, the buffer, or other water-soluble components, the optically active α-substituted β-amino acid derivative can be extracted using a hydrophobic organic solvent into an organic layer, which is then separated from the aqueous layer.

Examples of the hydrophobic organic solvent include: ethers such as tert-butyl methyl ether and isopropyl ether; hydrocarbons such as toluene, hexane, cyclohexane, heptane, octane, and isooctane; halogenated hydrocarbons such as dichloromethane, dichloroethane, chloroform, chlorobenzene, and ortho-dichlorobenzene; and esters such as ethyl acetate, methyl acetate, and butyl acetate. In the case of using these hydrophobic organic solvents during the reaction, the reaction solution after the completion of the reaction may be subjected directly to separation operation provided that it can be separated into an organic layer and an aqueous layer. Alternatively, in the case where no hydrophobic organic solvent is used during the reaction or the reaction solution is not easy to separate into an organic layer and an aqueous layer due to the small amount of the hydrophobic organic solvent or water used or cannot be easy to separate due to the small amount of water used, the hydrophobic organic solvent or water or the like can be added appropriately, followed by separation. The amount of the hydrophobic organic solvent used is not particularly limited and is in the range of usually approximately 0.1 to 200 parts by weight, preferably approximately 0.2 to 100 parts by weight, with respect to 1 part by weight of the optical isomers of the α-substituted β-amino acid ester derivative.

The pH during the extraction of the compound of interest is usually in the range of approximately 2 to 10, preferably in the range of approximately 4 to 8.

An acid and a base may be used appropriately for adjusting the solution to the pH. In the case where the extraction of the compound of interest from the aqueous layer is insufficient, the same extraction and separation operation may be repeated several times. Moreover, in the case where the removal of the water-soluble components from the organic layer is insufficient, the same extraction and separation operation may be repeated several times, as described above.

The residual ester thus separated from the asymmetric hydrolysate carboxylic acid by extraction can be isolated by distilling off the organic solvent in the oil layer. The obtained optically active α-substituted β-amino acid ester derivative can be subjected to racemization treatment and thereby recycled as an optical isomer mixture of the α-substituted β-amino acid ester derivative.

The residual ester thus isolated by distilling off the organic solvent in the oil layer may be further purified by column chromatography or the like.

After the extraction, the optically active α-substituted β-amino acid derivative, which is an asymmetric hydrolysate, is contained in the separated aqueous layer, and this can be taken easily out of the aqueous layer, for example, by distilling off water or extracting it using an organic solvent after neutralization treatment. The separated α-substituted n-amino acid derivative can be isolated by distilling off the organic solvent in the oil layer.

The optically active α-substituted n-amino acid derivative thus obtained may be further purified by purification operation such as column chromatography, recrystallization, or reprecipitation. In the purification operation such as recrystallization or reprecipitation, the optically active α-substituted β-amino acid derivative may be further converted to a salt using an appropriate base, and this salt is then purified by recrystallization or reprecipitation. The purified salt may be converted back to the optically active α-substituted n-amino acid derivative by an appropriate method.

The enzyme of the present invention or the transformant which produces the enzyme or processed product of the transformant can be used in various forms in the method described above.

Examples of the specific forms can include the cultures of the transformant of the present invention, the processed product of this transformant, cell-free extract solutions, semi-purified proteins, purified proteins, and immobilized forms thereof. In this context, examples of the treated product of the transformant can include freeze-dried transformants, organic solvent-treated transformants, dried transformants, milled transformants, transformant autolysates, sonicated transformants, transformant extracts, and alkali-treated transformants. Examples of the method for obtaining the immobilized forms can include a carrier binding method (a method involving adsorbing the enzyme of the present invention or the like onto an inorganic carrier (silica gel, ceramic, etc.), cellulose, an ion-exchange resin, or the like) and an entrapment method (a method involving allowing the enzyme of the present invention or the like to be trapped in the network structure of a polymer such as polyacrylamide, sulfur-containing polysaccharide gel (e.g. carrageenan gel), alginic acid gel, or agar gel).

In consideration of industrial production using the transformant of the present invention, a method using the processed product in which the transformant is dead is more preferable than a method using the untreated transformant, because of being less limited by production equipment. Examples of the microorganism killing treatment method for this purpose can include physical sterilization methods (heating, drying, freezing, light beam, ultrasonic waves, filtration, and electrification) and sterilization methods using chemicals (alkali, acid, halogen, oxidizing agents, sulfur, boron, arsenic, metal, alcohol, phenol, amine, sulfide, ether, aldehyde, ketone, cyanogen, and antibiotics). It is generally preferred to select, of these sterilization methods, a treatment method that less affects the reaction system by residues, contamination, etc. while the reductase activity of the enzyme of the present invention is prevented as much as possible from being deactivated.

The enzyme modification method of the present invention is a method for modifying an enzyme comprising the amino acid sequence of SEQ ID NO: 1, comprising a step of substituting the tyrosine at position 277 in the amino acid sequence of SEQ ID NO: 1 with alanine, tryptophan, isoleucine, or histidine.

The step included in the enzyme modification method of the present invention can be performed according to methods similar to those in the descriptions above (e.g., the descriptions about the preparation of the enzyme of the present invention and the polynucleotide of the present invention) and Examples described later (e.g., Preparation of polynucleotide of the present invention: site-directed mutagenesis).

The polynucleotide modification method of the present invention is a method for modifying a polynucleotide comprising a nucleotide sequence encoding the amino acid sequence of SEQ ID NO: 1, comprising a step of substituting the codon encoding tyrosine at positions 829 to 831 in the nucleotide sequence encoding the amino acid sequence of SEQ ID NO: 1 with a codon encoding alanine, tryptophan, isoleucine, or histidine.

The step included in the polynucleotide modification method of the present invention can be performed according to methods similar to those in the descriptions above (e.g., the descriptions about the preparation of the enzyme of the present invention and the polynucleotide of the present invention) and Examples described later (e.g., Preparation of the polynucleotide of the present invention: site-directed mutagenesis).

EXAMPLE

Hereinafter, the present invention will be described further specifically with reference to Examples. However, the present invention is not limited to these.

For methods for gene cloning and plasmid construction, methods described in "Molecular Cloning: A Laboratory Manual 2nd edition" (1989), Cold Spring Harbor Laboratory Press, ISBN 0-87969-309-6, "Current Protocols in Molecular Biology" (1987), John Wiley & Sons, Inc. ISBN 0-471-50338-X, etc. can be used as reference. Hereinafter, steps such as cloning will be described in detail.

Example 1

Preparation of the Polynucleotide of the Present Invention: Site-Directed Mutagenesis (1-1) Site-Directed Mutagenesis Operation Synthetic oligonucleotides as shown in SEQ ID NOs: 2 to 9 were synthesized as primers for mutagenesis so that the tyrosine at position 277 can be replaced with alanine, tryptophan, isoleucine, or histidine. The amino acids after introducing mutagenesis and the corresponding SEQ ID NOs and nucleotide sequences regarding the primers for mutagenesis are shown in Table 1.

TABLE 1

| SEQ ID NO | Substituting amino acid | Nucleotide sequence |
|---|---|---|
| 2 (Sense primer) | Alanine | GACGCGTCGTTCGCCGACCTCAACTAC |
| 3 (Antisense primer) | Alanine | GTAGTTGAGGTCGGCGAACGACGCGTC |
| 4 (Sense primer) | Tryptophan | GACGCGTCGTTCTGGGACCTCAACTAC |
| 5 (Antisense primer) | Tryptophan | GTAGTTGAGGTCCCAGAACGACGCGTC |
| 6 (Sense primer) | Isoleucine | GACGCGTCGTTCATCGACCTCAACTAC |
| 7 (Antisense primer) | Isoleucine | GTAGTTGAGGTCGATGAACGACGCGTC |
| 8 (Sense primer) | Histidine | GACGCGTCGTTCCACGACCTCAACTAC |
| 9 (Antisense primer) | Histidine | GTAGTTGAGGTCGTGGAACGACGCGTC |

The expression plasmid: pCC101 described in Japanese Patent No. 3875283 was used as a template to perform PCR according to reaction solution composition and reaction conditions shown below using the oligonucleotide shown by SEQ ID NO: 2 and the oligonucleotide shown by SEQ ID NO: 3 as primers and using QuickChange II Site-Directed Mutagenesis Kit manufactured by Stratagene Corp. The obtained PCR reaction solution is referred to as a PCR reaction solution (A).
[Reaction Solution Composition]
pCC101 vector solution 1.7 µl
dNTP mix (included in the Kit) 1 µl
Sense primer (50 µM) 0.4 µl
Antisense primer (50 µM) 0.4 µl
10× buffer (included in the Kit) 5 µl
PfuUltra (included in the Kit) 1 µl
Ultrapure water 41.5 µl
[PCR Reaction Conditions]
A container containing the reaction solution having the reaction solution composition as described above was placed in PERKIN ELMER-GeneAmp PCR System 2400 and subjected to incubation at 95° C. for 1 minute; incubation consisting of 12 cycles each including 95° C. for 50 seconds, subsequently 55° C. for 1 minute and 68° C. for 5 minutes; and incubation at 4° C.

1 µl of DpnI restriction enzyme (included in the Kit) was added to the obtained PCR reaction solution (A) and then incubated at 37° C. for 1 hour. The obtained incubation solution was used to transform E. coli JM109. In the same way as described above, PCR was carried out using the oligonucleotides of SEQ ID NOs: 4 and 5, the oligonucleotides of SEQ ID NOs: 6 and 7, or the oligonucleotides of SEQ ID NOs: 8 and 9, instead of using oligonucleotides of SEQ ID NOs: 2 and 3. In the same way as described above, 1 µl of DpnI restriction enzyme was added to the obtained PCR reaction solution followed by incubation at 37° C. for 1 hour, and E. coli JM109 was transformed with the obtained solution.

(1-2) Sequencing of the Variant

A vector was extracted from each of the transformants obtained in (1-1), and the mutation site was then sequenced by a dideoxy method to confirm that the nucleotide sequence was mutated as designed. In this way, transformants (i.e., the transformants of the present invention) containing each of the expression plasmid of the present invention (the vectors of the present invention: 277A, 277W, 277I, and 277H) were obtained.

Example 2

Production of Enzyme of the Present Invention by Transformant Microorganisms

Four types of recombinant E. coli obtained by Example 1, each of which was transformed with the plasmids for expressing the enzymes of the present invention, were separately inoculated to LB media (1% tryptone, 0.5% yeast extracts, and 0.5% NaCl), and then cultured at 37° C. IPTG (isopropyl-β-D-thiogalactopyranoside) was added at a final concentration of 1 mM thereto during the logarithmic growth phase to induce the expression of the hydrolases (enzymes of the present invention). After the completion of the culture, the bacterial cells were collected by centrifugation (8000 g, 10 min., 4° C.) and homogenized using glass beads. Then, a portion of a centrifugation supernatant of each homogenate solution was subjected to SDS-PAGE. As a result, the hydrolases were observed as main bands at the molecular weight position of approximately 40000 in all of these four types of samples, and the enzymes of the present invention were highly expressed in all the E. coli samples.

Examples 3 to 6

Production of Optically Active
2-n-butyl-3-[(N-benzyloxy-N-formyl)amino]propanoic Acid The amounts shown in Table 2 of the enzymatic solutions containing each of the four types of enzymes of the present invention obtained by Example 2 were separately weighed into containers, and 5 mL of 0.1 M potassium phosphate buffer solution (pH 7.0) and 40.0 mg of the optical isomer mixture (racemate) of 2-n-butyl-3-[(N-benzyloxy-N-formyl) amino]propanoic acid ethyl ester were added thereto. Each of these solutions was stirred at 25° C. for 48 hours, and 1 mL of 3.4% aqueous phosphoric acid solution and 10 mL of tert-butyl methyl ether were then added thereto and mixed. The mixture was left standing, and the tert-butyl methyl ether layer was then analyzed for its optical purity by high-performance liquid chromatography [column: CHIRALPAK AD-H, 4.6 mmφ×25 cm, 5 μm (manufactured by Daicel Corp.)] and analyzed for its chemical purity by high-performance liquid chromatography [column: Cadenza CD-18, 4.6 mmφ×15 cm, 3 μm (manufactured by Imtakt Corp.)] to determine the conversion rate and enantiomeric excess of the obtained optically active 2-n-butyl-3-[(N-benzyloxy-N-formyl)amino]propanoic acid. The results are shown in Table 2.

TABLE 2

| Example | Enzyme | Amount of enzyme (mg) | Conversion rate (%) | Enantiomeric excess (% ee) |
|---|---|---|---|---|
| 3 | 277A | 201.0 | 45.3 | 97.0 |
| 4 | 277W | 200.4 | 63.6 | 56.5 |
| 5 | 277I | 200.6 | 51.0 | 99.6 |
| 6 | 277H | 201.2 | 61.1 | 73.7 |

Conversion rate (%) = Amount of product/(Amount of substrate + Amount of product) × 100

Enantiomeric excess (% ee) = (A − B)/(A + B) × 100 (A and B represent the amounts of the corresponding enantiomers, wherein A > B).

INDUSTRIAL APPLICABILITY

The present invention can provide, for example, a hydrolase having excellent optical selectivity, which is used in organic synthesis reaction for producing, for example, compounds that are available for an active ingredient in pharmaceuticals or agricultural chemicals, or intermediates thereof, particularly, optically active compounds or intermediates thereof.

The invention claimed is:

1. An isolated enzyme of the following having the properties of (a) or (b):
   (a) an enzyme comprising the amino acid sequence of SEQ ID NO:1 at least from position 1 to position 362, wherein the tyrosine at position 277 of SEQ ID NO:1 is substituted with alanine, tryptophan, isoleucine, or histidine, and having the ability to hydrolyze a substrate; or
   (b) an enzyme comprising the amino acid sequence of SEQ ID NO:1 at least from position 1 to position 362, wherein the tyrosine at position 277 of SEQ ID NO:1 is substituted with an amino acid other than tyrosine, and having the ability to hydrolyze a substrate.

2. A polynucleotide comprising a nucleotide sequence encoding the amino acid sequence of the enzyme according to claim 1.

3. A vector comprising the polynucleotide according to claim 2.

4. A transformant into which the polynucleotide according to claim 2 has been introduced.

5. A transformant comprising the vector according to claim 3.

6. A method for producing an enzyme, comprising culturing the transformant according to claim 4 or 5.

7. A method for modifying an enzyme having the ability to hydrolyze a substrate, comprising a step of substituting the tyrosine at position 277 in the amino acid sequence of SEQ ID NO: 1 with alanine, tryptophan, isoleucine, or histidine.

8. A method for modifying a polynucleotide comprising a nucleotide sequence encoding an enzyme having the ability to hydrolyze a substrate, comprising a step of substituting the tyrosine-encoding codon at positions 829 to 831 in the nucleotide sequence encoding the amino acid sequence of SEQ ID NO:1 with a codon encoding alanine, tryptophan, isoleucine, or histidine.

\* \* \* \* \*

SEQUENCE LISTING

```
<160> NUMBER OF SEQ ID NOS: 11

<210> SEQ ID NO 1
<211> LENGTH: 370
<212> TYPE: PRT
<213> ORGANISM: Chromobacterium

<400> SEQUENCE: 1

Met Thr Leu Phe Asp Gly Ile Thr Ser Arg Ile Val Asp Thr Asp Arg
1               5                   10                  15

Leu Thr Val Asn Ile Leu Glu Arg Ala Ala Asp Asp Pro Gln Thr Pro
            20                  25                  30

Pro Asp Arg Thr Val Val Phe Val His Gly Asn Val Ser Ser Ala Leu
        35                  40                  45

Phe Trp Gln Glu Ile Met Gln Asp Leu Pro Ser Asp Leu Arg Ala Ile
    50                  55                  60

Ala Val Asp Leu Arg Gly Phe Gly Gly Ser Glu His Ala Pro Val Asp
65                  70                  75                  80

Ala Thr Arg Gly Val Arg Asp Phe Ser Asp Asp Leu His Ala Thr Leu
                85                  90                  95

Glu Ala Leu Asp Ile Pro Val Ala His Leu Val Gly Trp Ser Met Gly
            100                 105                 110

Gly Gly Val Val Met Gln Tyr Ala Leu Asp His Pro Val Leu Ser Leu
        115                 120                 125

Thr Leu Gln Ser Pro Val Ser Pro Tyr Gly Phe Gly Gly Thr Arg Arg
    130                 135                 140

Asp Gly Ser Arg Leu Thr Asp Asp Ala Gly Cys Gly Gly Gly Gly Gly
145                 150                 155                 160

Ala Asn Pro Asp Phe Ile Gln Arg Leu Ile Asp His Asp Thr Ser Asp
                165                 170                 175

Asp Ala Gln Thr Ser Pro Arg Ser Val Phe Arg Ala Gly Tyr Val Ala
            180                 185                 190

Ser Asp Tyr Thr Thr Asp His Glu Asp Val Trp Val Glu Ser Met Leu
```

```
                195                 200                 205
Thr Thr Ser Thr Ala Asp Gly Asn Tyr Pro Gly Asp Ala Val Pro Ser
    210                 215                 220

Asp Asn Trp Pro Gly Phe Ala Ala Gly Arg His Gly Val Leu Asn Thr
225                 230                 235                 240

Met Ala Pro Gln Tyr Phe Asp Val Ser Gly Ile Val Asp Leu Ala Glu
                245                 250                 255

Lys Pro Pro Ile Leu Trp Ile His Gly Thr Ala Asp Ala Ile Val Ser
            260                 265                 270

Asp Ala Ser Phe Tyr Asp Leu Asn Tyr Leu Gly Gln Leu Gly Ile Val
        275                 280                 285

Pro Gly Trp Pro Gly Glu Asp Val Ala Pro Ala Gln Glu Met Val Ser
290                 295                 300

Gln Thr Arg Asp Val Leu Gly Arg Tyr Ala Ala Gly Gly Gly Thr Val
305                 310                 315                 320

Thr Glu Val Ala Val Glu Gly Ala Gly His Ser Ala His Leu Glu Arg
                325                 330                 335

Pro Ala Val Phe Arg His Ala Leu Leu Glu Ile Ile Gly Tyr Val Gly
            340                 345                 350

Ala Ala Ala Asp Pro Ala Pro Pro Thr Glu Ala Ile Ile Ile Arg Ser
        355                 360                 365

Ala Asp
    370

<210> SEQ ID NO 2
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 2
gacgcgtcgt tcgccgacct caactac                                          27

<210> SEQ ID NO 3
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 3
gtagttgagg tcggcgaacg acgcgtc                                          27

<210> SEQ ID NO 4
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 4
gacgcgtcgt tctgggacct caactac                                          27

<210> SEQ ID NO 5
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 5
```

```
gtagttgagg tcccagaacg acgcgtc                                          27
```

<210> SEQ ID NO 6
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 6

```
gacgcgtcgt tcatcgacct caactac                                          27
```

<210> SEQ ID NO 7
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 7

```
gtagttgagg tcgatgaacg acgcgtc                                          27
```

<210> SEQ ID NO 8
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 8

```
gacgcgtcgt tccacgacct caactac                                          27
```

<210> SEQ ID NO 9
<211> LENGTH: 27
<212> TYPE: DNA
<213> ORGANISM: artificial sequence
<220> FEATURE:
<223> OTHER INFORMATION: Designed oligonucleotide primer for PCR

<400> SEQUENCE: 9

```
gtagttgagg tcgtggaacg acgcgtc                                          27
```

<210> SEQ ID NO 10
<211> LENGTH: 1110
<212> TYPE: DNA
<213> ORGANISM: Chromobacterium

<400> SEQUENCE: 10

```
atgaccctgt tcgacggcat cacgtctcgc atcgtcgaca ccgaccgcct gaccgtgaac       60
atcctggagc gcgcggccga cgacccgcag accccgcccg accgcacggt cgtgttcgtc      120
cacgggaatg tgtcctccgc gctgttctgg caggagatca tgcaggacct gccgagcgac      180
ctgcgcgcca tcgcggtcga cctgcgcggc ttcggcggct cggagcacgc gccggtcgac      240
gccacccgcg cgtccgcga  cttcagcgac gatctgcacg cgaccctcga ggcgctcgac      300
atcccggtcg cgcatctggt cggctggtcg atgggcggcg cgtcgtcat  gcagtatgcc      360
ctcgaccacc cggtgctgag cctgaccctg cagtcgccgg tgtcgcccta cggcttcggc      420
ggcacccgcc gtgacggctc acgcctcacc gacgacgatg ccggctgcgg tggcggcggt      480
gcgaaccccg acttcatcca gcgcctcatc gaccacgaca cctccgacga tgcgcagacc      540
tcgcccggga gcgtcttccg cgccggctac gtcgcctcgg actacaccac cgaccacgag      600
gacgtgtggg tcgaatcgat gctcaccacg tccaccgccg acggaaacta ccccggcgat      660
```

```
gcggtgccga gcgacaactg gccgggcttc gccgccggcc gccacggcgt gctgaacacc      720
atggccccgc agtacttcga tgtgtcgggg attgtcgacc tggccgagaa gcctccgatc      780
ctgtggatcc acggcaccgc ggacgcgatc gtctccgacg cgtcgttcta cgacctcaac      840
tacctcggcc agctgggcat cgtccccggc tggcccggcg aagacgtcgc gcccgcgcag      900
gagatggtgt cgcagacccg cgatgtcctc ggccgctacg ctgcgggcgg cggaacggtc      960
accgaggtcg ccgtcgaggg cgcgggccac tccgcgcacc tggagcgtcc cgcggtgttc     1020
cgccacgcgc tgctcgagat catcggctac gtcggcgcgg cggccgaccc cgccccgccg     1080
accgaggcga tcatcatccg ctccgccgac                                      1110
```

<210> SEQ ID NO 11
<211> LENGTH: 1110
<212> TYPE: DNA
<213> ORGANISM: artificial sequence
<220> FEATURE:
<223> OTHER INFORMATION: Designed polynucleotide encoding an asymmetric
      hydrolase derived from Chromobacterium

<400> SEQUENCE: 11

```
atgactctgt tcgatggtat cacttcgcga atcgtagata ctgatcgtct gactgttaac       60
atcctggaac gtgcggccga cgacccgcag accccgcccg accgcacggt cgtgttcgtc      120
cacgggaatg tgtcctccgc gctgttctgg caggagatca tgcaggacct gccgagcgac      180
ctgcgcgcca tcgcggtcga cctgcgcggc ttcggcggct cggagcacgc gccggtcgac      240
gccacccgcg gcgtccgcga cttcagcgac gatctgcacg cgaccctcga ggcgctcgac      300
atcccggtcg cgcatctggt cggctggtcg atgggcggcg cgtcgtcat gcagtatgcc       360 ctcgaccacc cggtgctgag cctgaccctg cagtcgccgg tgtcgcccta cggcttcggc      420
ggcacccgcc gtgacggctc acgcctcacc gacgacgatg ccggctgcgg tggcggcggt      480
gcgaaccccg acttcatcca gcgcctcatc gaccacgaca cctccgacga tgcgcagacc      540
tcgccccgga gcgtcttccg cgccggctac gtcgcctcgg actacaccac cgaccacgag      600
gacgtgtggg tcgaatcgat gctcaccacg tccaccgccg acgaaaacta ccccggcgat      660
gcggtgccga gcgacaactg gccgggcttc gccgccggcc gccacggcgt gctgaacacc      720
atggccccgc agtacttcga tgtgtcgggg attgtcgacc tggccgagaa gcctccgatc      780
ctgtggatcc acggcaccgc ggacgcgatc gtctccgacg cgtcgttcta cgacctcaac      840
tacctcggcc agctgggcat cgtccccggc tggcccggcg aagacgtcgc gcccgcgcag      900
gagatggtgt cgcagacccg cgatgtcctc ggccgctacg ctgcgggcgg cggaacggtc      960
accgaggtcg ccgtcgaggg cgcgggccac tccgcgcacc tggagcgtcc cgcggtgttc     1020
cgccacgcgc tgctcgagat catcggctac gtcggcgcgg cggccgaccc cgccccgccg     1080
accgaggcga tcatcatccg ctccgccgac                                      1110
```